United States Patent
Zemskov et al.

(10) Patent No.: US 11,243,282 B2
(45) Date of Patent: Feb. 8, 2022

(54) METHODS AND SYSTEMS FOR A FLOATING CABLE TRAP

(71) Applicant: GE Precision Healthcare LLC, Milwaukee, WI (US)

(72) Inventors: Aleksey Zemskov, Solon, OH (US); Victor Taracila, Beachwood, OH (US); Taylan Dalveren, North Ridgeville, OH (US); Fraser John Laing Robb, Aurora, OH (US); Limin Feng, Solon, OH (US)

(73) Assignee: GE Precision Healthcare LLC, Milwaukee, WI (US)

( * ) Notice: Subject to any disclaimer, the term of this patent is extended or adjusted under 35 U.S.C. 154(b) by 228 days.

(21) Appl. No.: 16/578,197

(22) Filed: Sep. 20, 2019

(65) Prior Publication Data
US 2021/0088609 A1   Mar. 25, 2021

(51) Int. Cl.
*G01R 33/36* (2006.01)
*A61B 5/055* (2006.01)

(52) U.S. Cl.
CPC .......... *G01R 33/3685* (2013.01); *A61B 5/055* (2013.01)

(58) Field of Classification Search
CPC .. G01R 33/3685; G01R 33/3621; A61B 5/055
See application file for complete search history.

(56) References Cited

U.S. PATENT DOCUMENTS

| | | |
|---|---|---|
| 10,185,002 B2 | 1/2019 | Stormont et al. |
| 10,209,328 B2 | 2/2019 | Taracila et al. |
| 2017/0343627 A1 | 11/2017 | Taracila et al. |
| 2019/0265316 A1* | 8/2019 | Wynn ................ G01R 33/3685 |

FOREIGN PATENT DOCUMENTS

WO    WO-2010003215 A1 *  1/2010  ......... H01B 11/1813

* cited by examiner

*Primary Examiner* — Susan S Lee
(74) *Attorney, Agent, or Firm* — McCoy Russell LLP

(57) ABSTRACT

Various methods and systems are provided for a current trap. In one example, the current trap has a spiral core made of a nonconductive material, a coiled wire having a plurality of turns wound around the spiral core, and one or more tuning capacitors physically attached to the spiral core and electrically connected to the coiled wire to form a resonance circuitry with the coiled wire.

20 Claims, 11 Drawing Sheets

METHODS AND SYSTEMS FOR A
FLOATING CABLE TRAP

FIELD

Embodiments of the subject matter disclosed herein relate to magnetic resonance imaging, and more particularly, to a current trap for a magnetic resonance imaging system.

BACKGROUND

Magnetic resonance imaging (MRI) is a medical imaging modality that can create images of the inside of a human body without using x-rays or other ionizing radiation. MM systems include a superconducting magnet to create a strong, uniform, static magnetic field $B_0$. Exposure of a human body, or part of a human body, to the magnetic field $B_0$, induces polarization of hydrogen nuclear spin in tissue water. The nuclei are excited by a radio frequency signal and upon relaxation to a rest energy state, energy is released as an RF signal which may be transformed into an image.

An MM system utilizes RF coils to transmit RF excitations and/or receive MR signals. Shielded coil-interfacing cables may be used to transmit signals between the RF coils and other aspects of a processing system of the MRI system. For example, the coil-interfacing cables may transmit signals to control the RF coils and/or to receive signals from the RF coils. The coil-interfacing cables may be subjected to electro-magnetic fields and as a result, transmitter-driven common mode currents may adversely affect coil tuning, coil-to-coil coupling in phased array coils, inhomogeneity in generated images, and/or unpredictable heating of components.

Common mode traps, or baluns, providing high common mode impedances, may be used to mitigate the effect of transmitter-driven currents. Conventionally, grounded baluns may be coupled to the coil-interfacing cables to block the induced currents. However, coupling of the baluns to the coil-interfacing cables may demand a complex soldering process. The soldering process may expose conductors in the coil-interfacing cables to high temperatures, leading to degradation of the conductors.

BRIEF DESCRIPTION

In one embodiment, a current trap includes spiral core made of a nonconductive material, a coiled wire having a plurality of turns wound around the spiral core, and one or more tuning capacitors physically attached to the spiral core and electrically connected to the coiled wire to form a resonance circuitry with the coiled wire. In this way, soldering of the current trap assembly to coil-interfacing cables is not demanded and the current trap assembly may located anywhere along the cables.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIGS. 3-10 are drawn approximately to scale.

DETAILED DESCRIPTION

Figure 2:
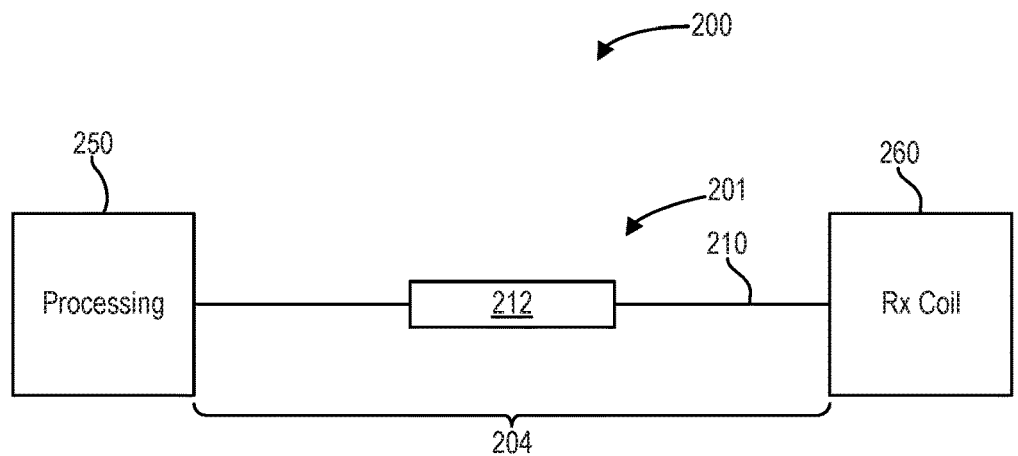
FIG. 2 is a block schematic diagram of a current trap assembly which may be implemented in the Mill system according to an exemplary embodiment of the disclosure.
Figure 3:
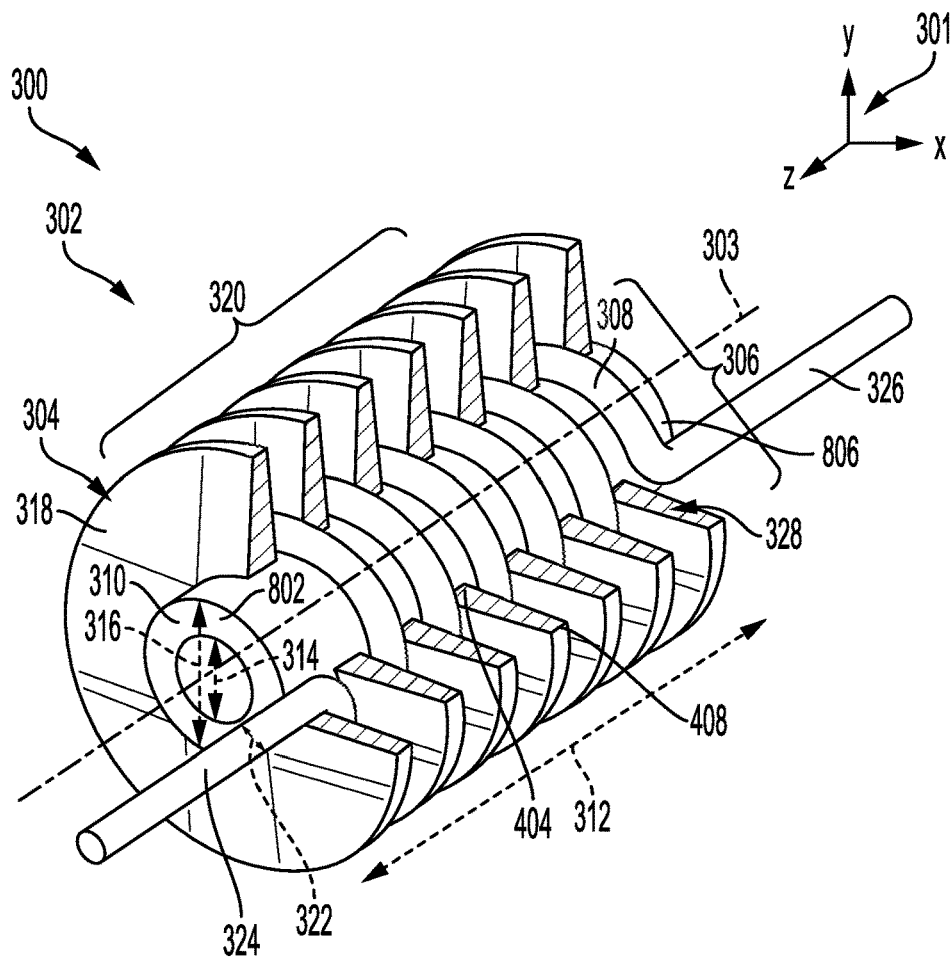
FIG. 3 is a perspective view of a current trap with a portion of a spiral core of the current trap removed according to an exemplary embodiment of the disclosure.
Figure 4:
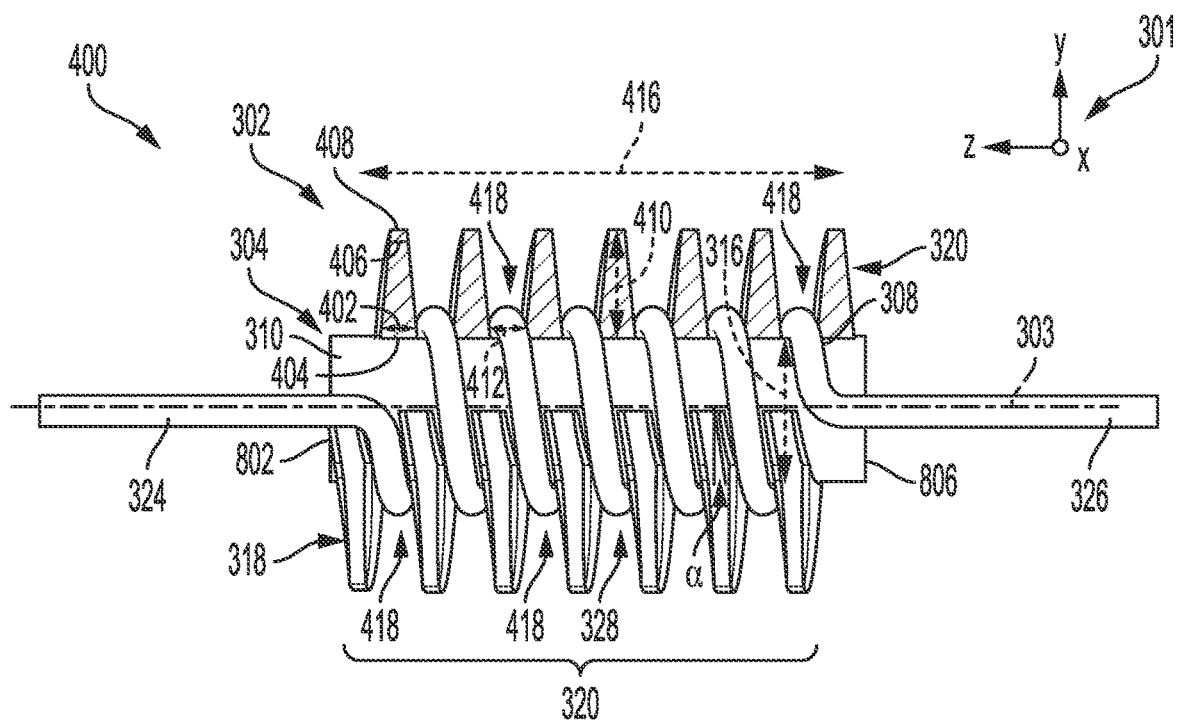
FIG. 4 is a side view of the current trap of FIG. 3.
Figure 5:
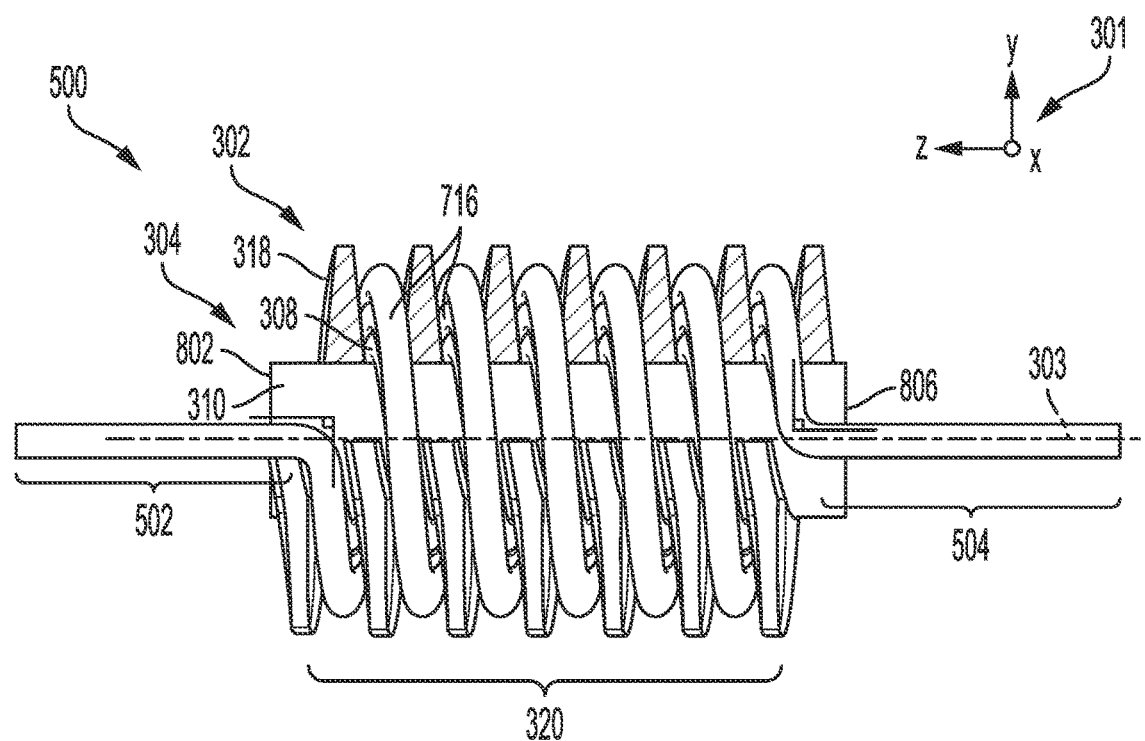
FIG. 5 is a side view of a floating current trap assembly with a portion of a spiral cores removed, showing the current trap coupled to cables according to an exemplary embodiment of the disclosure.
Figure 6:
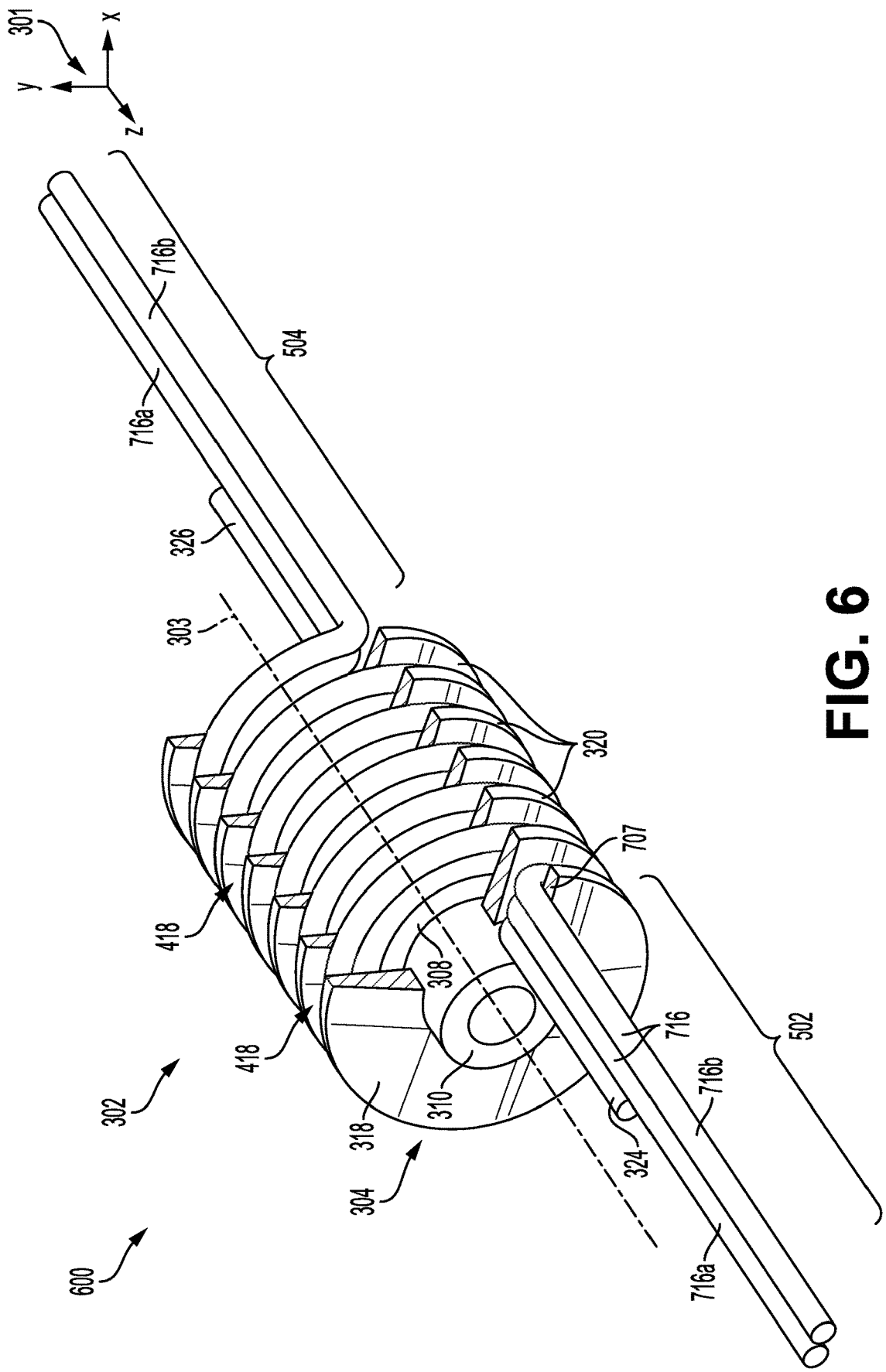
FIG. 6 is a perspective view of the floating current trap assembly of FIG. 5.
Figure 7:
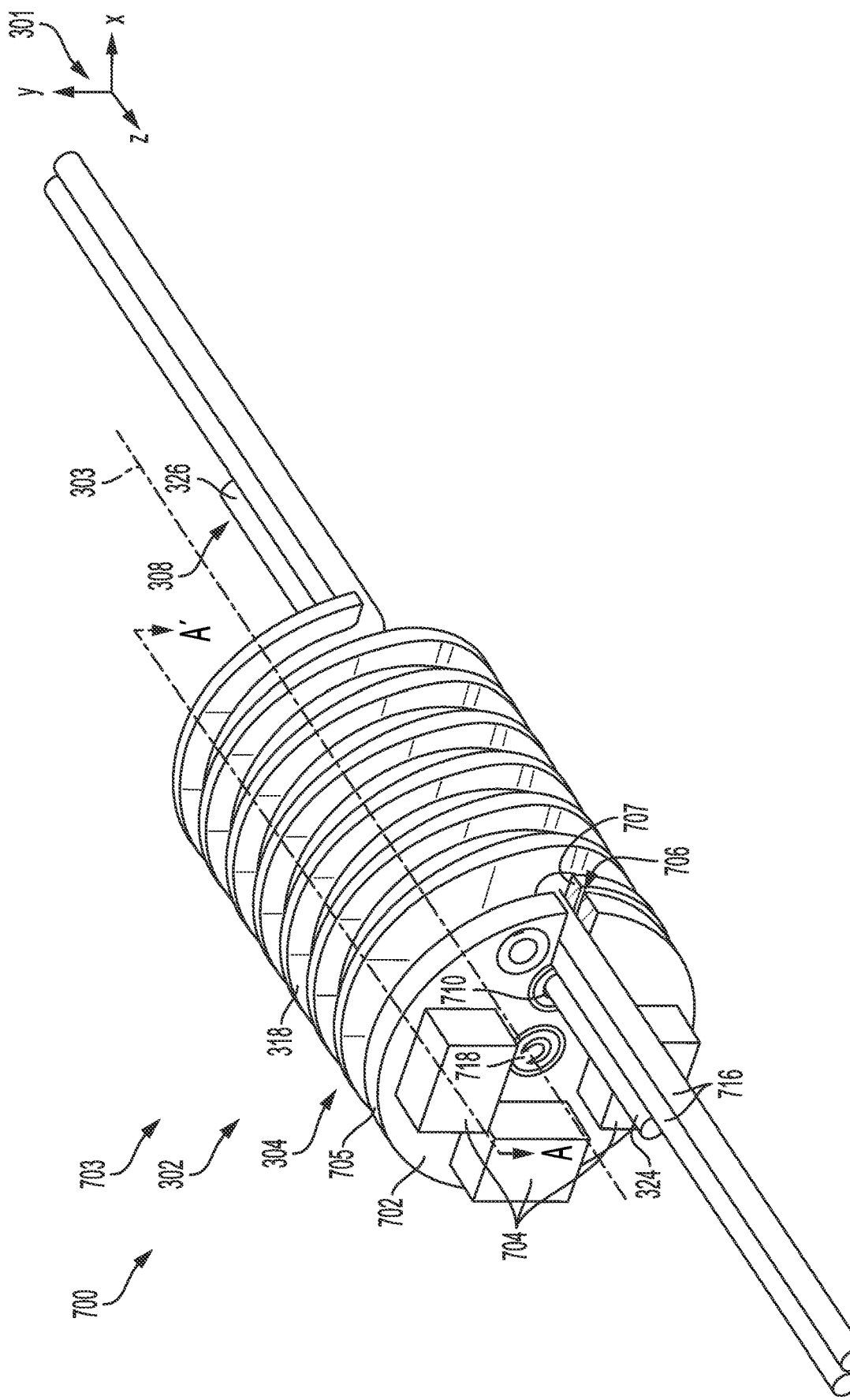
FIG. 7 is a perspective view of a floating current trap assembly according to an exemplary embodiment of the disclosure.
Figure 8:
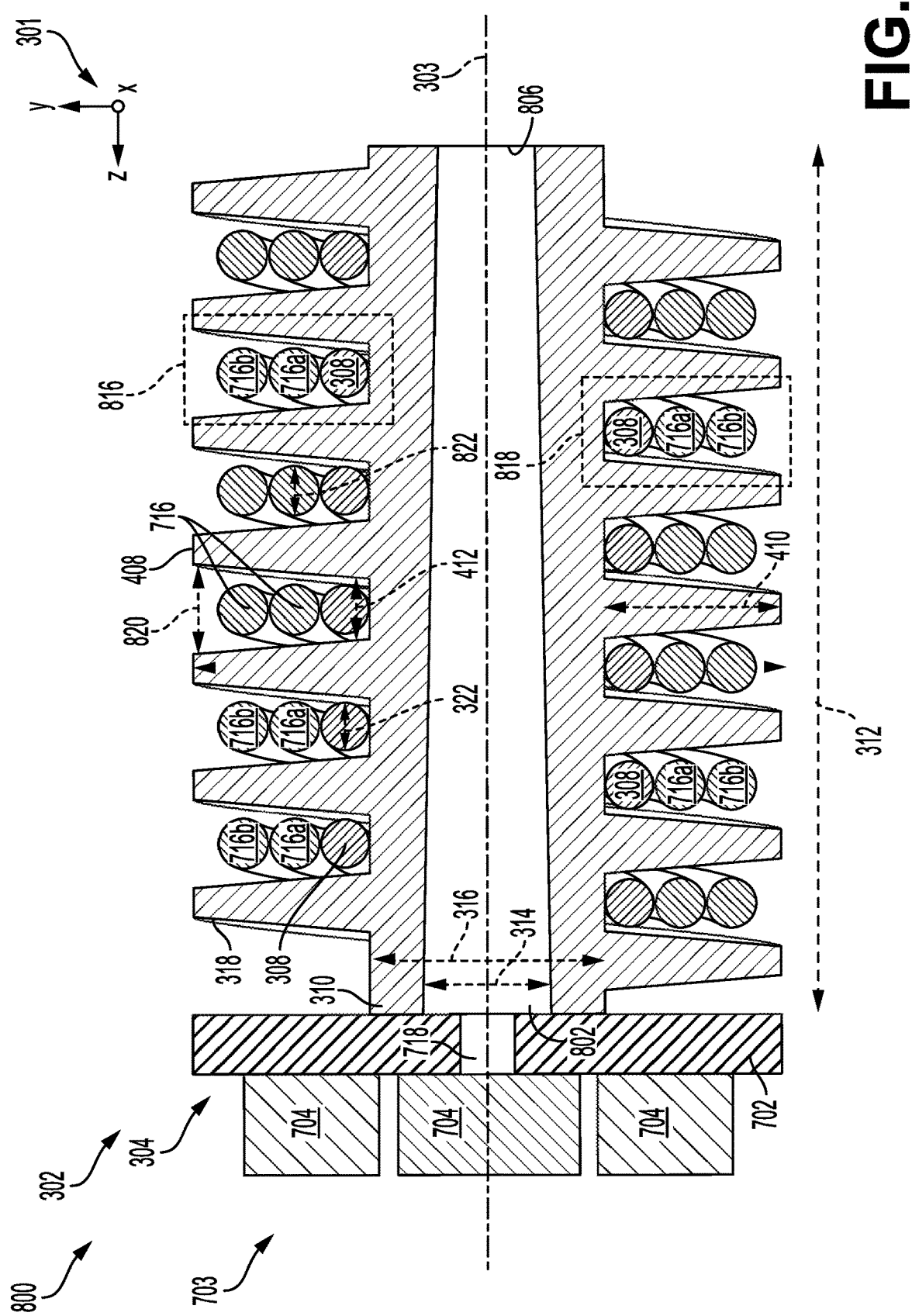
FIG. 8 is a cross-section of the floating current trap assembly of FIG. 7.
Figure 9:
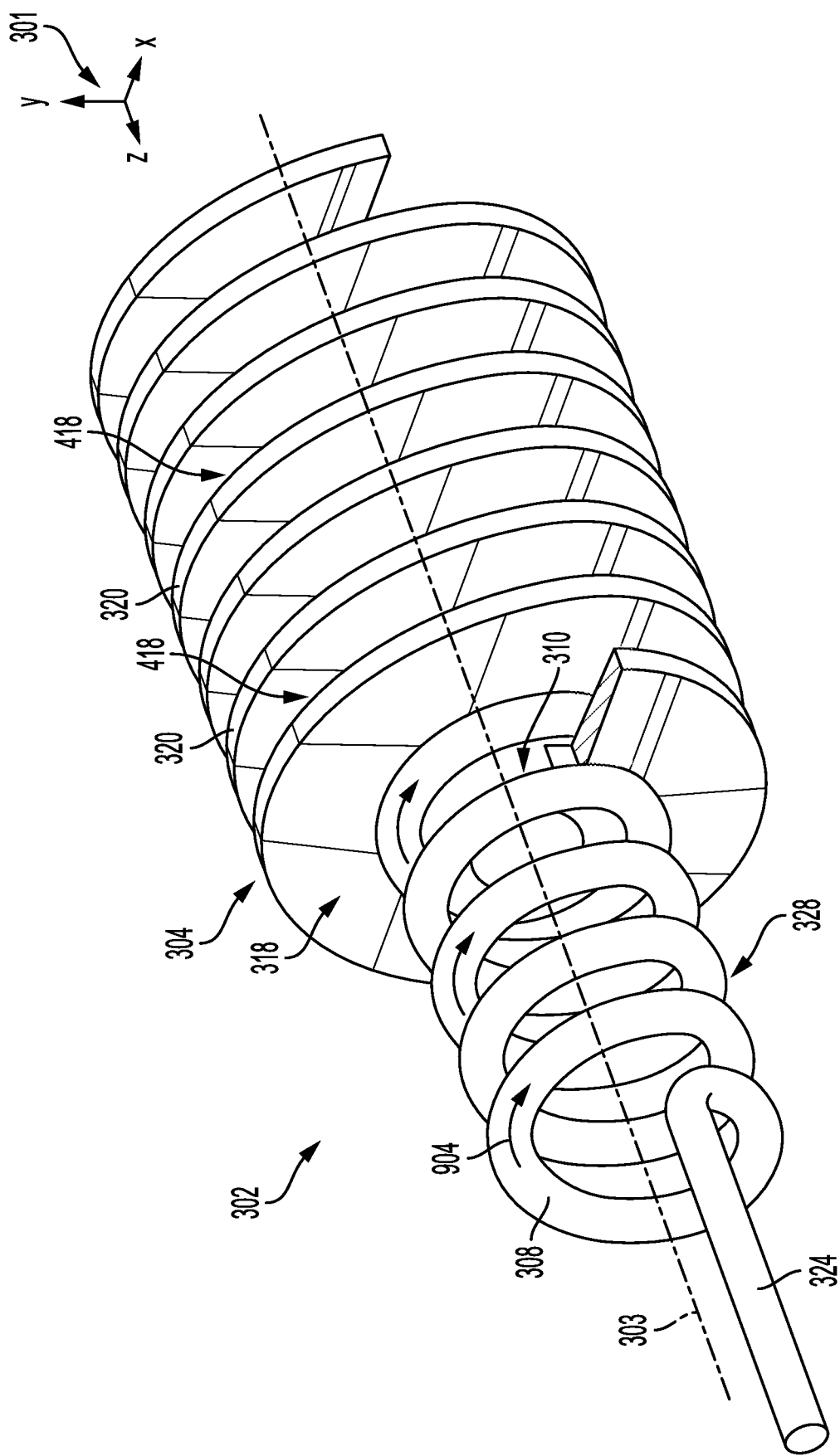
FIG. 9 is a perspective view of a coiled wire being assembled with a spiral core according to an exemplary embodiment of the disclosure.
Figure 10:
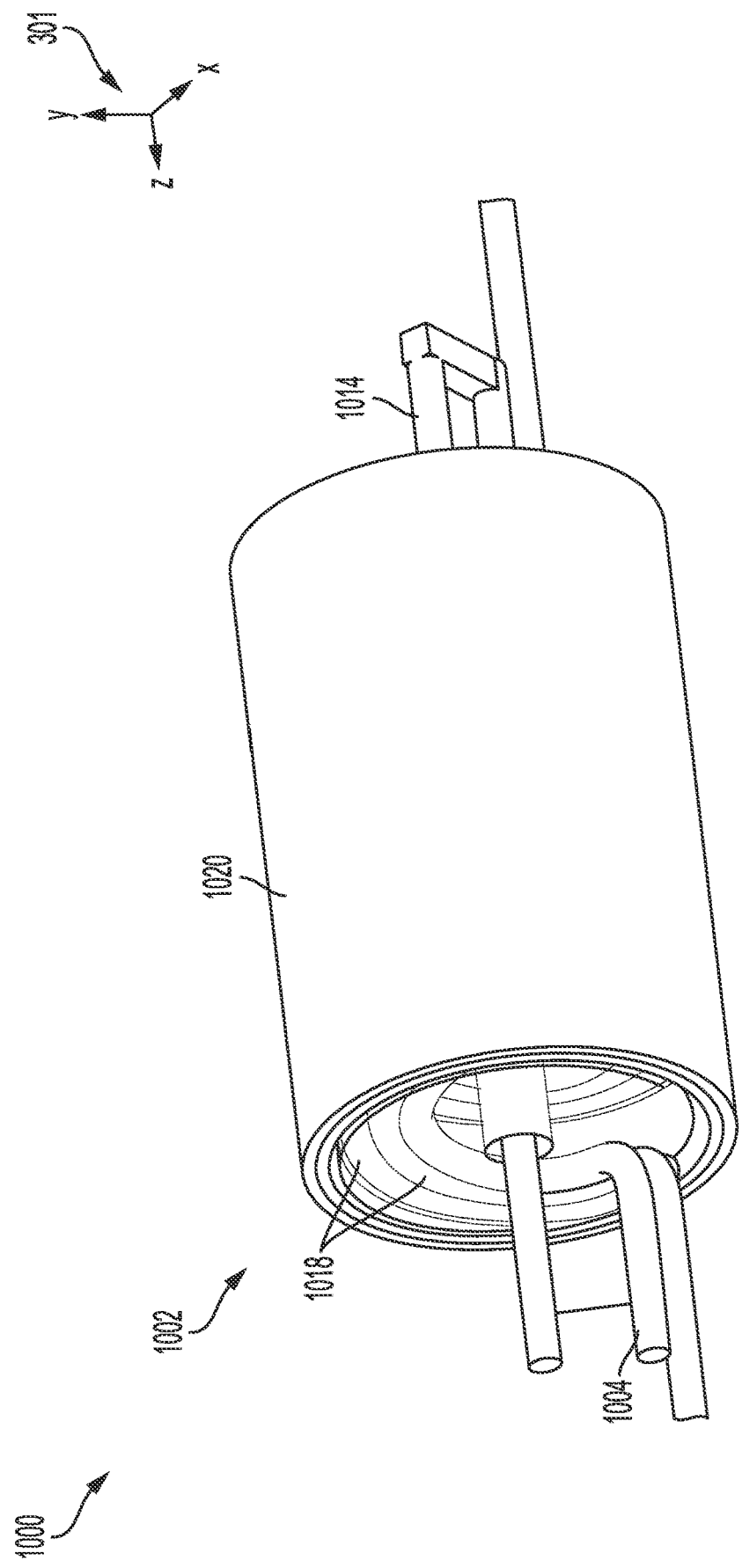
FIG. 10 is a perspective view of a shielded current trap according to an exemplary embodiment of the disclosure.
Figure 11:
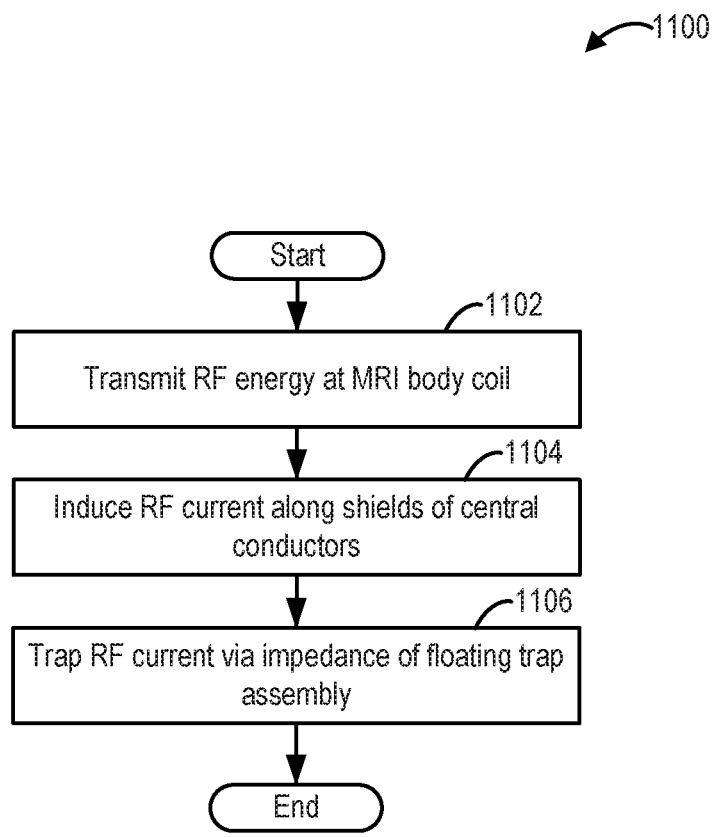
FIG. 11 is a high-level block diagram illustrating an example of a routine for a floating current trap assembly according to an exemplary embodiment of the disclosure.
Figure 12:
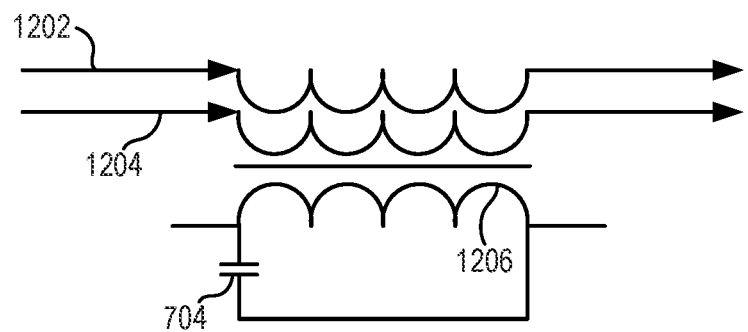
FIG. 12 is a schematic electrical circuit diagram of a floating current trap assembly according to an exemplary embodiment of the disclosure.
Figure 13:
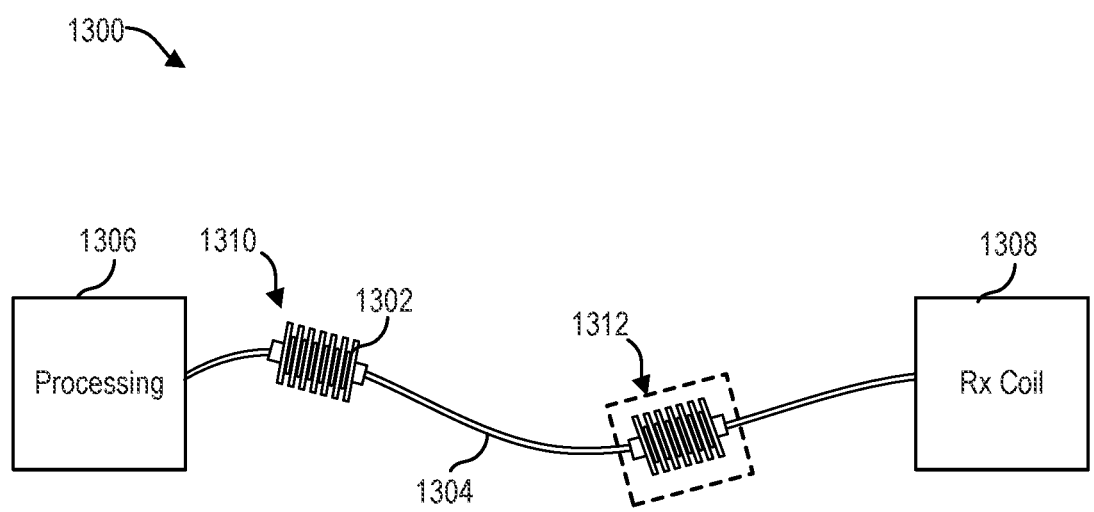
FIG. 13 illustrates an example of relocation of a floating current trap assembly along a coil-interfacing cable of an MRI system according to an exemplary embodiment of the disclosure.
Figure 14:
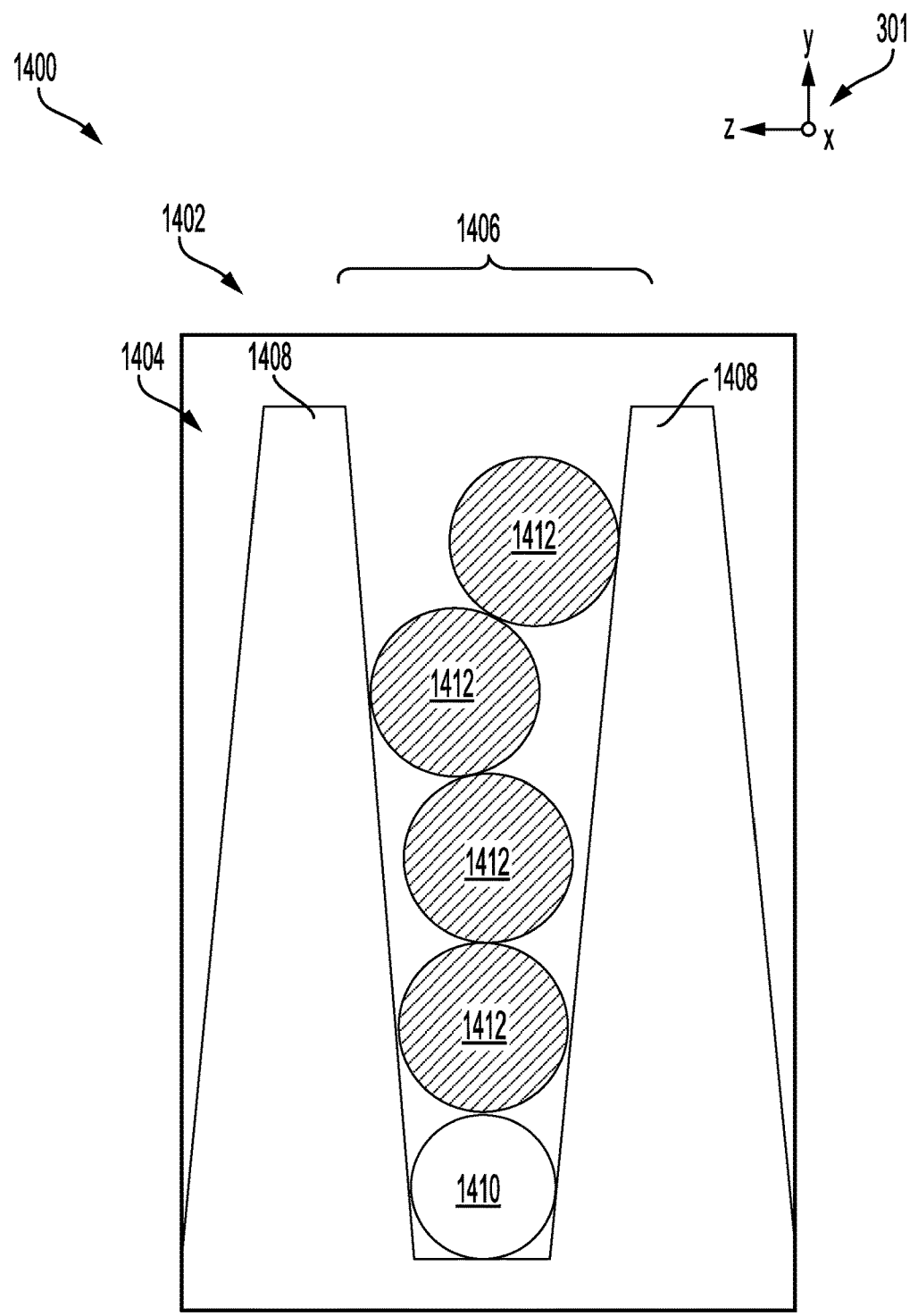
FIG. 14 is a detailed view of a current trap coupled to four cables.

The following description relates to various embodiments for a current trap for MRI systems. In particular, systems are provided for a floating spiral configuration for a current trap for an MRI system, such as the MM system illustrated in FIG. 1. Herein, a floating trap may be defined as a trap that may be removably coupled to cables of the MRI system by mechanical engagement and without additional processes to secure the trap to the cables, such as soldering. Furthermore, coupling the floating trap to the cables, unlike non-floating current traps, does not demand cutting of the cables, thus allowing a position of the floating trap to be readily reconfigured along the cables. As shown in FIG. 2, a current trap may be arranged along a communication cable configured to receive MR data. The current trap may be a floating trap as depicted in FIGS. 3 and 4. The current trap may be assembled by engaging a coiled wire with a spiral core, as shown in FIG. 9. The current trap may be configured to engage with cables of the MRI system by winding the cables around the spiral core, as illustrated in FIGS. 5 and 6. As illustrated in FIG. 14, the current trap may be coupled to up to four cables. A floating trap assembly is shown in FIG. 7 and a cross-section of the assembly is shown in FIG. 8. The current trap may be further covered with a shield, as illustrated in FIG. 10, when the current trap is to be positioned proximate to a patient. A routine for blocking transmission-induced currents along cable of an MRI system by implementing the floating trap is depicted in FIG. 11. A schematic of an electrical circuit of the floating trap is shown in FIG. 12 and a repositioning of the floating trap along a cable of an MRI system is illustrated in FIG. 13.

FIGS. 3-10 and 14 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Figure 1:
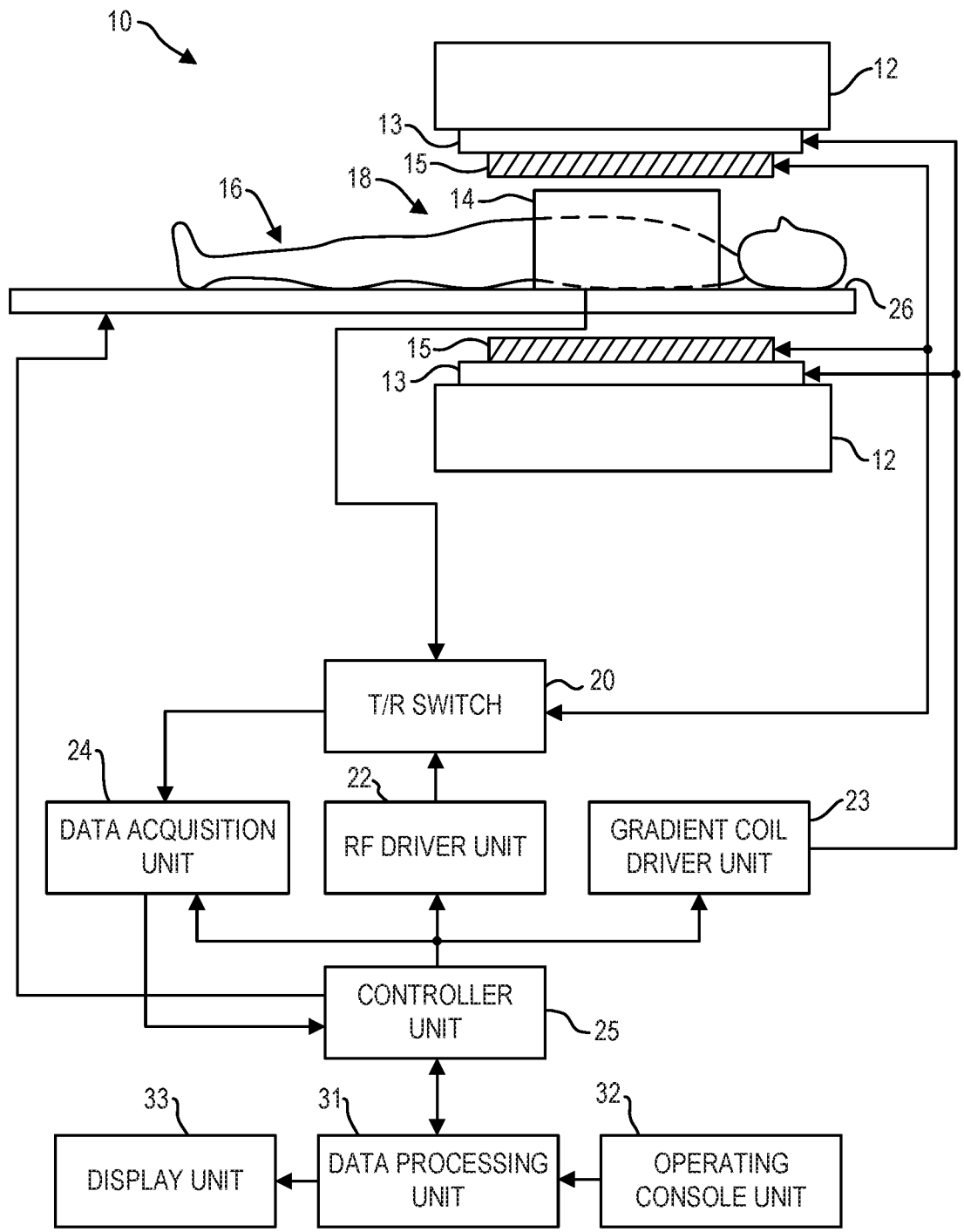
FIG. 1 is a block diagram of an Mill system according to an exemplary embodiment of the disclosure.

FIG. 1 illustrates a magnetic resonance imaging (MM) apparatus 10 that includes a magnetostatic field magnet unit 12, a gradient coil unit 13, an RF coil unit 14, an RF body coil unit 15, a transmit/receive (T/R) switch 20, an RF driver unit 22, a gradient coil driver unit 23, a data acquisition unit 24, a controller unit 25, a patient bed 26, a data processing unit 31, an operating console unit 32, and a display unit 33. The Mill apparatus 10 transmits electromagnetic pulse signals to a subject 16 placed in an imaging space 18 with a magnetostatic field formed to perform a scan for obtaining magnetic resonance signals from the subject 16 to reconstruct an image based on the magnetic resonance signals thus obtained by the scan.

The magnetostatic field magnet unit 12 includes, for example, typically an annular superconducting magnet, which is mounted within a toroidal vacuum vessel. The magnet defines a cylindrical space surrounding the subject 16, and generates a constant primary magnetostatic field.

The MM apparatus 10 also includes a gradient coil unit 13 that forms a gradient magnetic field in the imaging space 18 so as to provide the magnetic resonance signals received by the RF coil unit 14 with three-dimensional positional information. The gradient coil unit 13 includes three gradient coil systems, each of which generates a gradient magnetic field which inclines into one of three spatial axes perpendicular to each other, and generates a gradient field in each of frequency encoding direction, phase encoding direction, and slice selection direction in accordance with the imaging condition.

The RF coil unit 14 is disposed, for example, to enclose the region to be imaged of the subject 16. In the static magnetic field space or imaging space 18 where a static magnetic field is formed by the magnetostatic field magnet unit 12, the RF coil unit 14 may transmit, based on a control signal from the controller unit 25, an RF pulse to the subject 16. This excites a spin of protons in the subject 16. The RF coil unit 14 may also receive magnetic resonance signals generated when the proton spin thus excited in the subject 16 returns into alignment with the initial magnetization vector. The RF coil unit 14 may transmit RF excitation and receive MR signal using the same RF coil.

The RF body coil unit 15 is disposed, for example, to enclose the imaging space 18, and produces RF pulses within the imaging space 18 to excite the nuclei. In contrast to the RF coil unit 14, which may be easily disconnected from the MR apparatus 10 and replaced with another RF coil unit, the RF body coil unit 15 is fixedly attached and connected to the MR apparatus 10.

The T/R switch 20 can selectively connect the RF body coil unit 15 to the data acquisition unit 24 when operating in receive mode, and to the RF driver unit 22 when operating in transmit mode. Similarly, the T/R switch 20 can selectively connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode, a receive-only mode, or a transmit-receive mode. The coils of the local RF coil unit 14 may be configured to operate in a transmit-receive mode or a receive-only mode.

The RF driver unit 22 may include a gate modulator (not shown), an RF power amplifier (not shown), and an RF oscillator (not shown). The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 14.

The gradient coil driver unit 23 drives the gradient coil unit 13 based on a control signal from the controller unit 25 and thereby generates a gradient magnetic field in the imaging space 18. The gradient coil driver unit 23 may include three systems of driver circuits (not shown) corresponding to the three gradient coil systems included in the gradient coil unit 13.

The data acquisition unit 24 may include a preamplifier (not shown), a phase detector (not shown), and an analog/digital converter (not shown). The phase detector phase detects, using the output from the RF oscillator of the RF driver unit 22 as a reference signal, the magnetic resonance signals received from the RF coil unit 14 and amplified by the preamplifier, and outputs the phase-detected analog magnetic resonance signals to the analog/digital converter for conversion into digital signals. The digital signals thus obtained are output to the data processing unit 31.

The MM apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to an MRI scan.

The operating console unit 32 may include user input devices such as a keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The data processing unit 31 includes a computer and a recording medium on which a program to be executed by the computer to perform data processing is recorded. The data processing unit 31 is connected to the controller unit 25 and performs data processing based on control signals received from the controller unit 25. The data processing unit 31 is also connected to the data acquisition unit 24 and generates spectrum data by applying various image processing operations to the magnetic resonance signals output from the data acquisition unit 24.

The display unit 33 includes a display device and displays an image and/or other information on the display screen of the display device based on control signals received from the controller unit 25. The display unit 33 displays, for example, scanning parameters. The display unit 33 also displays an MR image of the subject 16 generated by the data processing unit 31.

During a scan, coil-interfacing cables (not shown) may be used to transmit signals between the RF coils (e.g., RF coil unit 14) and other aspects of the processing system (e.g., data acquisition unit 24, controller unit 25, and so on), for example to control the RF coils and/or to receive information from the RF coils. In some embodiments, the coil-interfacing cables are integrated into the RF coil unit 14. The coil-interfacing cables may be disposed within the bore or imaging space 18 of the MRI apparatus 10 and subjected to electro-magnetic fields produced and used by the MRI apparatus 10. The cables may be subject to transmitter driven common mode currents which create field distortions and/or unpredictable heating of components. Baluns or common mode traps that provide high common mode impedances may be utilized to mitigate the effect of transmitter driven currents. Various embodiments of such common mode traps and common mode trap assemblies are described further herein.

FIG. 2 illustrates a block schematic diagram of a common mode trap assembly 200 or balun assembly 200. The balun assembly 200 may be configured, for example, for use in the bore of an MRI system, such as the MRI apparatus 10 described herein above. For example, in the illustrated embodiment, the balun assembly 200 is configured as a transmission cable 201 configured for transmission of signals between a processing unit (or controller) 250 and a receive coil 260 of an MM system. In some embodiments, the transmission cable 201 is integrated into the receive coil 260 and becomes part of it. The receive coil 260 further includes one or more coil elements coupled to the transmission cable, as known in the art.

In the illustrated embodiment, the transmission cable 201 (or balun assembly 200) includes a central conductor 210 and at least one balun 212. The central conductor 210 in the illustrated embodiment has a length 204, and is configured to transmit a signal between the MRI receive coil 260 and at least one processor of an MRI system (e.g., processing unit 250). The central conductor 210 may include one or more of a ribbon conductor, a wire, or a coaxial cable bundle, for example.

The depicted balun 212, as seen in FIG. 2, extends along at least a portion of the length 204 of the central conductor 210. In the illustrated embodiment, balun 212 does not extend along the entire length 204. However, in other embodiments, the balun 212 may extend along the entire length 204, or substantially along the entire length 204.

The balun 212 is configured to provide an impedance to the receive transmitter driven currents of an MM system. The balun 212 in various embodiments provides high common mode impedances. For example, the balun 212 may include a resonant circuit and/or one or more resonant components to provide a high impedance at or near a desired frequency or within a target frequency range. It may be noted that the balun 212 may also be referred to as a choke by those in the art.

The balun 212 may be tuned to have a resonant frequency near an operating frequency of the MRI system. As used herein, a balun may be understood as having a resonant frequency near an operating frequency when the resonant frequency defines or corresponds to a band that includes the operating frequency, or when the resonant frequency is close enough to the operating frequency to provide on-frequency blocking, or to provide a blocking impedance at the operating frequency.

In conventional designs, the balun has a central opening through which the central conductor passes and the balun is usually soldered to the central conductor. Such soldering process may be complex and may expose the central conductor to high temperatures. The central conductor, adapted for RF applications, may be sensitive to heat and soldering the central conductor may result in degradation of the central conductor. The present disclosure describes an implementation of a balun that may be installed without soldering or any special complex process. Additionally, the balun may be removed and reinstalled without causing any wire degradation.

An exemplary embodiment of a balun 302 is shown in FIGS. 3-9. The balun 302 may be a current trap 302 shown in FIGS. 3 and 4 in a first view 300 and a second view 400, respectively, without being coupled to any cables yet. Furthermore, the current trap 302 may be an unshielded current trap. A set of reference axes 301 are provided, indicating a y-axis, an x-axis, and a z-axis. The current trap has a central axis 303 which is parallel with the z-axis.

The current trap 302 may be a generally cylindrical structure formed of two portions: a spiral core 304, and a coiled wire 308. The spiral core 304 may be formed of a rigid, durable, nonconductive (e.g., insulating) material, such as plastic, and provides a frame for the current trap 302. A central tube 310 of the spiral core 304 may extend along an entire length 312 of the spiral core 304 along the central axis 303. The length 312 of the spiral core 304 may be different depending on an application of the current trap 302. For example, a diameter and length of a cable to which the current trap 302 is coupled may affect the length 312 of the spiral core. As an example, the length 312 of the spiral core 304 may be 3.5 cm. An inner diameter 314 of the central tube 310 may be, for example, 0.2-0.5 cm while an outer diameter 316 of the central tube 310 may be 0.4-0.7 cm. The inner diameter 314 and the outer diameter 316 may be uniform along the length 312 of the spiral core 304. Alternatively, as shown in a cross-section 800 in FIG. 8, the inner diameter 314 may taper between a first end 802 and a second end 806 of the central tube 310 for plastic piece tooling. However, in other embodiments, the inner diameter 314 may remain uniform between the first end 802 and the second end 806.

A spiral rib 318 may be disposed at an outer surface of the central tube 310, protruding radially outwards from the central axis 303. The spiral rib 318 may provide insulation between each turn of the coiled wire 308, where each turn is a full 360 degree rotation around the central axis 303. In other words, each turn of the coiled wire 308 is spaced away from adjacent turns by the spiral rib 318, thereby electrically insulating each turn. The spiral core 304 may be fabricated, by injection molding, for example, so that the spiral rib 318 and the central tube 310 are made as one piece. The spiral rib 318 may have a trapezoidal cross-section, e.g., when the cross-section is taken along the y-z plane as shown in FIG. 4. Therein, a width 402 of the spiral rib 318, defined along the z-axis, at a base 404 of the spiral rib 318 is greater than a width 406 of the spiral rib 318 at an outer edge or tip 408 of the spiral rib 318.

A height 410 of the spiral rib 318 may be equal to or greater than a sum of a diameter 322 of the coiled wire 308 plus a diameter of each cable coupled to the current trap 302. For example, as shown in FIG. 8, the height 410 is equal to or greater than the sum of the diameter 322 of the coiled wire, a diameter of a first cable 716a and a diameter of a second cable 716b. The spiral rib 318 protrudes radially outwards, away from the central tube 310, and coils around the central tube 310 to form a plurality of layers 320. The plurality of layers 320 are continuous with one another but are seen individually in the cross-sectional view in FIG. 4.

The height 410 of the spiral rib 318 remains substantially uniform along the length 312 of the spiral core 304. Thus, each of the plurality of layers 320 are similar in shape and size. The uniform height of the spiral rib 318 results in a cylindrical outer geometry of the spiral core 304. As shown in FIG. 4, the plurality of layers 320 are spaced uniformly apart along the length 312 of the spiral core 304. A distance between each of the plurality of layers 320 at the base 404 of each layer may be a pitch 412 of the spiral rib 318. The pitch 412 may be similar to, narrower, or wider than the width 402 of the spiral rib 318 at the base 404 of the spiral rib 318.

The pitch 412 of the spiral rib 318 may be configured to accommodate winding of the coiled wire 308 so that the coiled wire 308 is inserted between each of the plurality of layers 320 at the base 404 of each of the plurality of layers 320. As such, the pitch 412 of the spiral rib 318 may be similar to or larger than the diameter 322 (shown in FIG. 3) of the coiled wire 308. The pitch 412 of the spiral rib 318 may be different according to the thickness of the coiled wire 308. For example, if a thicker coiled wire 308 is to be inserted into the spiral core 304, the pitch 412 of the spiral rib 318 may be made larger. Conversely, if a thinner coiled wire 308 is to be inserted, the pitch 412 may be made smaller. The length 312 of the spiral core 304 may also be varied if a specific pitch and a specific number of the plurality of layers 320 is desired. Furthermore, a helix angle α, as shown in FIG. 4, indicates an angle of a spiraling of the spiral rib 318 relative to the y-axis.

The coiled wire 308 is wound around the central tube 310 along the spiral rib 318. In some embodiments, the coiled wire 308 includes a first straight section 324 and a second straight section 326, and a central portion 328, positioned between the first straight section 324 and the second straight section 326 and coiled around the central tube 310 of the spiral core 304. In some embodiments, the coiled wire 308 includes only the central portion 328, which forms an inductor and enables the current trap 302 to interact with coil-interfacing cables through electromagnetic induction. The central portion 328 of the coiled wire 308 generates an electromagnetic field when a shield current flows through the coil-interfacing cables, which impedes the shield current via a resonance circuitry of the current trap 302, as described further below. The coiled wire 308 may be a conductor made of any appropriate conductive material, such as copper, aluminum, etc., but not ferromagnetic materials.

A length 416 of the central portion 328, as shown in FIG. 4, may be similar to or shorter than the length 312 of the spiral core 304. The central portion 328 may have a number of turns equal to or fewer than a number of spaces 418 in between the plurality of layers 320 of the spiral core 304. In FIG. 4, the central portion 328 has six turns, corresponding to six spaces 418 between the plurality of layers 320. However, other numbers of turns of the central portion 328 of the coiled wire 308 and of spaces 418 between the plurality of layers 320 have been contemplated, such as 4, 7, 8, etc.

As described above, the central portion 328 of the coiled wire 308 is in contact with and wraps around the central tube 310 of the spiral core 304. The central portion 328 has a helical configuration and each turn of the central portion 328 coils around the central tube 310 of the spiral core 304 along a uniform angle relative to the y-axis, which may be equal or close to the helix angle α.

FIG. 9 shows the coiled wire 308 being coupled to the spiral core 304. The central portion 328 may be fed into the spaces 418 between the plurality of layers 320 by turning the coiled wire 308 in a rotational direction indicated by arrows 904. The coiled wire 308 may be rotated until all turns of the central portion 328 are engaged in the spaces 418. The engagement of the coiled wire 308 with spiral core 304 forces the turns of the coiled wire 308 to be spaced apart by the pitch 412 of the spiral core 304.

The current trap 302 may further include one or more tuning capacitors that form a resonance circuitry with the coiled wire 308 which functions as an inductor in the circuitry. A printed circuit board (PCB) 702 may carry the tuning capacitors, as shown in a perspective view 700 and in the cross-section view 800 of FIG. 8, taken along line A-A' of FIG. 7. The PCB 702 may carry a set of tuning capacitors 704, each tuning capacitor spaced apart from the other tuning capacitors 704 and arranged on an outward facing surface of the PCB 702, e.g., a surface of the PCB 702 facing away from the spiral core 304 of the current trap 302. The current trap 302 may be tuned by coupling a probe to the PCB 702 to adjust the impedance to block a target frequency, such as 127.7 MHz, before the current trap assembly 703 is coupled to the coil-interfacing cable. In other words, the current trap assembly 703 may be pre-tuned during manufacturing and provided to a user as a tuned, ready-to-use device.

The PCB 702 may be coupled to the first end 802 (as shown in FIG. 8) of the central tube 310 of the spiral core 304 by an adhesive. It will be appreciated that the PCB 702 may be similarly coupled to the second end 806 of the central tube 310 of the spiral core 304 without affecting a tuning capacity of the set of tuning capacitors 704. The PCB 702 may include a slot 706, as shown in FIG. 7 extending from an outer edge 705 of the PCB 702 towards the central axis 303 and terminating at a rounded end 710 disposed between the outer edge 705 of the PCB 702 and the central axis 303. The rounded end 710 of the slot may align with the first section 324 of the coiled wire 308 along the z-axis, allowing the first section 324 of the coiled wire 308 to extend through the rounded end 710. The rounded end 710 may be lined with a conductive material, such as a copper gasket, and functions as a first electrical connection end for the set of capacitors 704. In some embodiments, the rounded end 710 is made in contact with the first section 324 of the coiled wire 308 via soldering, to electrically couple the set of tuning capacitors 704 of the PCB 702 to the coiled wire 308 at one end.

The PCB 702 may also have a central aperture 718 aligned with the central axis 303 and extending entirely through a thickness of the PCB 702, as shown in FIG. 8, where the thickness is defined along the z-axis. A bus wire functions as a second electrical connection end for the set of capacitors 704 and passes through the central aperture 718 of the PCB 702. The bus wire continues to pass through the central tube 310 from the first end 802 all the way to the second end 806 and is made in contact with the second section 326 of the coiled wire 308 via soldering, to electrically couple the set of tuning capacitors 704 of the PCB 702 to the coiled wire 308 at another end.

The PCB 702 may be configured as a circular disc as shown in FIGS. 7 and 8. A variety of conductive tracks, pads and other features may be etched into laminated sheets of copper and electrical components, such as the set of tuning capacitors 704, may be soldered on to the PCB 702. The set of tuning capacitors 704 may be spaced away from one another. In some embodiments, the inductor formed by the coiled wire 308 is connected to the set of capacitors 704 by connecting two ends of the coiled wire 308 to two ends of the capacitor set 704 respectively, as described above.

One or more cables may be wound around the spiral core 304 and stacked on top of the coiled wire 308 to form a floating trap assembly. FIGS. 7 and 8 show two cables 716 wound around the spiral core 304 and stacked on top of the coiled wire 308. An equivalent electrical circuit diagram of this floating trap assembly is shown in FIG. 12. The inductor 1206 (e.g., central portion 328 of coiled wire 308) and the tuning capacitor(s) 704 form a resonance circuitry. Cables 1202 and 1204 (e.g., coil-interfacing cables in an MRI system) are coupled to the inductor 1206 via electromagnetic interaction. The resonance circuitry has a high impedance to shield currents generated in cables 1202 and 1204 and can reduce the shield currents through the electromagnetic coupling with cables 1202 and 1204.

The cables 716 may be coil-interfacing cables, curving around a first end 707 of the spiral rib 318 and extending through the slot 706, as shown in FIGS. 6-8. Each of the cables 716 may include a shield. The shield may be a common conductive layer, formed of a material such as braided strands of metal, a spirally wound metallic tape, a conducting polymer, etc., that circumferentially surrounds each of the cables 716. As such, the shield encloses one or more insulated conductors, e.g., wires, of each of the cables 716. Implementing each of the cables 716 with the shield may reduce electrical noise which may otherwise degrade electrical signals transmitted by the cables 716. The shield may also decrease electromagnetic radiation which may cause electromagnetic interference with other electrical devices.

The conductive nature of the shield may result in an increased likelihood of generation of shield currents on the cables 716, which may cause localized heating of the cables 716, distortion of MRI images, and adversely affect coil tuning. Thus equipping the MM system with at least one floating trap assembly 703 may circumvent the issues described above.

The coupling of the PCB 702 to the current trap 302 allows the floating trap assembly 703 to be tuned away from an MM system and independent of the MM system. Use of the floating trap assembly 703 may therefore be expedited by precluding a time-consuming tuning procedure. The tuning procedure may be performed during manufacturing of the floating trap assembly 703 where the set of tuning capacitors 704 may be adjusted to provide an impedance of the floating trap assembly 703 that blocks a resonant frequency of a shield current carried by the cables 716. Alternatively, the floating trap assembly 703 may be configured to block a range of frequencies to enable the floating trap assembly 703 to be used across a variety of systems with varying resonance frequencies to be impeded.

The cable(s) 716 may be wound around the spiral core 304 of the current trap 302 through the spaces 418 between the plurality of layers 320 of the spiral core 304, the spaces 418 shown in FIG. 4. The cable(s) 716 may be arranged so that the cables 716 are stacked along the y-axis within each of the spaces 418. The stacking of the cables 716 is shown in greater detail in FIGS. 5, 6 and 8. A side view 500 and a perspective view 600 of the current trap 302 coupled to the cables 716 is depicted in FIGS. 5 and 6, respectively. Similar to FIGS. 3-4, a section (e.g., indicated by bracket 306 in FIG. 3) of the spiral rib 318 of the spiral core 304 is removed for clarity. The cables 716 may be similar in diameter to the diameter 322 of the coiled wire 308 or may have diameters different from the coiled wire 308 or from one another in other examples.

A configuration of the cables 716, when coupled to the spiral core 304, may be similar to the configuration of the coiled wire 308. A first region 502 and a second region 504 of the cables 716, which are not coupled to the spiral core 304, may extend away from the spiral core 304 along the z-axis. The cables 716 may follow a similar geometry to the coiled wire 308 wrapping around the central portion 328 of the coiled wire 308 through the spaces 418 between the plurality of layers 320 along the helix angle α, as shown in FIG. 4 and extending away from the spiral core 304 at the first and second regions 502, 504, in opposite directions.

The stacking of the cables 716 and the coiled wire 308 along the spiral core 304 is further depicted in the cross-section 800 of FIG. 8. The cables 716 include the first cable 716a and the second cable 716b, as shown in a first dashed region 816. The first cable 716a is positioned directly adjacent to the coiled wire 308, in between the coiled wire 308 and the second cable 716b, as shown in the first and second regions 502, 504 of the cables 716 in FIG. 6. In other words, no other cables or objects are disposed between the first cable 716a and the coiled wire 308 along an entire length of the coiled wire 308.

As the cables 716 wind through the spiral core 304, the relative positioning of the first cable 716a, as shown in FIG. 8, is maintained in contact with the coiled wire 308 along the length 312 of the spiral core 304. In the first dashed region 816 of FIG. 8, the coiled wire 308 and the cables 716 are stacked along the y-axis, e.g., along a radial direction perpendicular to the central axis 303, with the first cable 716a on top of the coiled wire 308 and the second cable 716b on top of the first cable 716a. While the stacking of the coiled wire 308 and the cables 716 may be angled with respect to the y-axis, e.g., following the helix angle α as shown in FIG. 4, the coiled wire 308 and the cables 716 do not align parallel with the central axis 303 at any point along the spiral core 304.

A second dashed region 818 shows an arrangement of the coiled wire 308 and the cables 716 in an opposite side of the spiral core 304 from the first dashed region 816. The first cable 716a is positioned directly below the coiled wire 308 along the y-axis and the second cable 716b is positioned directly below the first cable 716a. Thus the relative positioning of the first cable 716a and second cable 716b is maintained along the spiral core 304 and around the spiral core 304.

Dimensions of the spaces 418 between the plurality of layers 320 of the spiral core 304 may be configured to accommodate cable diameters that differ from the diameter 322 of the coiled wire 308. The pitch 412 of the spiral rib 318 may be similar to the diameter 322 of the coiled wire 308. A width of the spaces 418 may increase along the y-axis towards the tip 408 of the spiral rib 318 (which are also tops 408 of the plurality of layers 320) so that a width 820 of the spaces 418 at the tops 408 of the spaces 418 is wider than the pitch 412 of the spiral core 304. The increase in width of the spaces 418 in a radial direction away from the central axis 303 enables a diameter 822 of each of the cables 716, which may be larger than the diameter 322 of the coiled wire 308, to fit within the spaces 418. However, the width 820 of the spaces 418 is maintained less than two times the diameter 822 of the cables 716 so that the cables may not shift.

The height 410 of the spiral rib 318 may be equal to or greater than a sum of the diameter 322 of the coiled rib 308 and the diameters 822 of the cables 716. Furthermore, the height 410 may be varied to accommodate more cables 716 than shown in FIGS. 5-7. The current trap 302 may be configured to couple to up to four cables 716, the cables 716 stacked similarly to the first and second cables 716a, 716b, as shown in FIG. 8, along the radial direction perpendicular to the central axis 303. An example of a current trap coupled to four cables is depicted in FIG. 14.

FIG. 14 shows a detailed view 1400 of a section of a current trap 1402 having a spiral core 1404 similarly configured to the spiral core 304 shown in FIGS. 3-9. A space 1406 between adjacent threads 1408 of the spiral core 1404 receives a coiled wire 1410 and four cables 1412. The cables 1412 are stacked on top, relative to the y-axis, of the coiled wire 1410 and on top of one another.

The floating trap assembly 703 may have several advantages over a conventional balun (e.g., non-floating). The coil-interfacing cables of the MRI system may be wrapped around the spiral core of the floating trap assembly without cutting the cables. Thus soldering of the floating trap assembly to the cables is not demanded, mitigating exposure of the cables to high temperature. As the floating trap assembly is a portable unit that is not anchored to any other structures, the floating trap assembly may be positioned anywhere along the cables without cutting the cables and may therefore be placed in convenient locations along the cables that allow the floating trap assembly to be readily accessed.

An example of how a floating trap assembly may be reconfigured along at least one coil-interfacing cable is depicted in a schematic diagram 1300 in FIG. 13. The current trap 1302 may be coupled to a cable 1304 extending between a processing unit 1306 and a receive coil 1308 of an MRI system. The current trap 1302 may be arranged at a first location 1310, closer to the processing unit 1306 than the receive coil 1308, and connected to the cable 1304 by winding the cable 1304 around a spiral core of the floating trap assembly 1302 on top of a coiled wire of the current trap 1302.

The floating trap assembly may be re-located to a second location 1312 along the cable 1304 by unwinding the cable 1304 from the spiral core of the current trap 1302 and moving the current trap 1302 along the cable, closer to the receive coil 1308. The current trap 1302 may be coupled to the cable 1304 by winding the cable 1304 around the spiral core of the current trap 1302. Furthermore, the floating trap assembly may be readily re-positioned to any point along the cable 1304 between the processing unit 1306 and the receive coil 1308.

Referring to FIG. 10, a shielded current trap 1002 is depicted in a perspective view 1000. Similar to the unshielded current trap shown in FIGS. 3-4, the shielded current trap 1002 may have a coiled wire 1004 coupled to a bus wire 1014 which functions as an electrical connection end for tuning capacitor(s). Additionally, the shielded current trap 1002 may be configured as a floating current trap. It will be appreciated that while the bus wire 1014 of FIG. 10 is not depicted in FIGS. 3-9 for brevity, the bus wire 1014 may be similarly coupled to the current trap 302 of FIGS. 3-9.

In addition to components of the unshielded current trap, the shielded current trap 1002 further comprises a shield 1020 enclosing the cables 1018. The shield 1020 is a hollow cylinder that encloses the spiral core, the coiled wire, and the cable. The shield 1020 may be formed of an electromagnetically insulating material such as plastic coated with an outer layer of copper tape. Furthermore, the shield 1020 may be provided as a sheet of the electromagnetically insulating material with a mechanism for coupling parallel edges of the sheet to one another. In this way, the cables 1018 may be first coiled around the spiral core and then the shield 1020 may be wrapped around the spiral core and maintained in the cylindrical geometry around the spiral core by fastening the parallel edges of the shield 1020 to one another. Implementing the shielded current trap 1002 with the shield 1020 may reduce the exposure of a patient to electromagnetic radiation.

FIG. 11 is a high-level block diagram illustrating an example method 1100 for blocking transmission-induced currents on one or more central conductors (e.g., coil-interfacing cables) by coupling the central conductors to a floating trap assembly, such as the floating trap assembly 703 of FIGS. 7 and 8, according to an embodiment of the disclosure. Prior to engagement with the central conductors, the floating trap assembly may be tuned to a resonance frequency that is equal or close to an operating frequency of an MRI system via tuning capacitors coupled to a printed circuit board of the floating trap assembly. The one or more central conductors may be successively wrapped around the floating trap assembly, as shown in FIGS. 5-8.

Method 1100 begins at 1102. At 1102, RF energy generated at a body coil of the MRI system is transmitted to the central conductors. The signal transmission generates a shield current which is carried along the shields of the central conductors at 1104. At 1106, the floating trap assembly traps the RF current at the central conductors. For example, a high impedance of the floating trap assembly, where the resonant frequency is pre-set (e.g., tuned) to the operating frequency of the MM system, reduces the shield current.

The technical effect of the disclosure may include improved performance of MM systems due to reduced interaction between transmission cables and coil elements. Another technical effect of the disclosure may include achieving desired impedance of a floating trap assembly via a single floating trap. Yet another technical effect of the disclosure may include positioning the floating trap assembly anywhere along the transmission cables. Yet another technical effect of the disclosure may include reducing a coil surface temperature relative to a feed board of an MRI system.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A current trap comprising:
   a spiral core made of a nonconductive material;
   a coiled wire having a plurality of turns wound around the spiral core; and
   one or more tuning capacitors physically attached to the spiral core and electrically connected to the coiled wire to form a resonance circuitry with the coiled wire.

2. The current trap of claim 1, wherein the spiral core comprises a central tube and a spiral rib protruding from the central tube, the spiral rib forms a plurality of spaces each for receiving one of the plurality of turns of the coiled wire.

3. The current trap of claim 2, further comprising a printed circuit board (PCB) attached to the spiral core, wherein the one or more tuning capacitors are carried by the PCB.

4. The current trap of claim 3, wherein the PCB is fixed to the spiral core through adhesive.

5. The current trap of claim 3, wherein a first electrical connection end for the one or more tuning capacitors is formed on the PCB and is electrically connected to a first end of the coiled wire.

6. The current trap of claim 5, wherein a second electrical connection end for the one or more tuning capacitor is a bus wire which passes through the central tube and is electrically connected to a second end of the coiled wire.

7. The current trap of claim 1, wherein the spiral core is made of plastic.

8. The current trap of claim 1, wherein the coiled wire is made of a non-ferromagnetic conductive material.

9. A floating current trap assembly comprising:
   a current trap comprising:
      a spiral core made of a nonconductive material;
      a coiled wire having a plurality of turns wound around the spiral core; and
      one or more tuning capacitors electrically connected to the coiled wire to form a resonance circuitry with the coiled wire; and
   one or more cables wound around the spiral core and stacked on the coiled wire, wherein the resonance circuitry has a high impedance for common mode currents carried by the one or more cables.

10. The floating current trap assembly of claim 9, wherein the one or more cables are coupled to the coiled wire though electromagnetic coupling.

11. The floating current trap assembly of claim 9, wherein a position of the current trap relative to the one or more cables is reconfigurable.

12. The floating current trap assembly of claim 11, wherein the position of the current trap is reconfigured by unwinding the one or more cables from the spiral core at a first position and rewinding the one or more cables on the spiral core at a second position.

13. The floating current trap assembly of claim 9, wherein the spiral core comprises a central tube and a spiral rib protruding from the central tube, the spiral rib forms a plurality of spaces each for receiving one of the plurality of turns of the coiled wire and the one or more cables.

14. The floating current trap assembly of claim 13, further comprising a printed circuit board (PCB) attached to the spiral core, wherein the one or more tuning capacitors are carried by the PCB.

15. The floating current trap assembly of claim 14, wherein a first electrical connection end for the one or more tuning capacitors is formed on the PCB and is electrically connected to a first end of the coiled wire, wherein a second electrical connection end for the one or more tuning capacitor is a bus wire which passes through the central tube and is electrically connected to a second end of the coiled wire.

16. A radio frequency (RF) coil unit for magnetic resonance imaging (MRI), the RF coil unit comprising:
   one or more RF coil elements;
   a coil-interfacing cable electrically coupled to the one or more RF coil elements; and
   a current trap comprising:
      a spiral core made of a nonconductive material;
      a coiled wire having a plurality of turns wound around the spiral core; and
      one or more tuning capacitors electrically connected to the coiled wire to form a resonance circuitry with the coiled wire,
   wherein the coil-interfacing cable is wound around the spiral core and stacked on the coiled wire.

17. The RF coil unit of claim 16, wherein the coiled wire is made of a non-ferromagnetic conductive material.

18. The RF coil unit of claim 16, wherein the coil-interfacing cable is coupled to the coiled wire through electromagnetic coupling, and wherein the resonance circuitry provides a high impedance for a common mode current carried by the coil-interfacing cable.

19. The RF coil unit of claim 16, wherein a position of the current trap relative to the coil-interfacing cable is reconfigurable.

20. The RF coil unit of claim 19, wherein the position of the current trap is reconfigured by unwinding the coil-interfacing cable from the spiral core at a first position and rewinding the coil-interfacing cable on the spiral core at a second position.

* * * * *